United States Patent

Drauz et al.

[11] Patent Number: 6,114,163
[45] Date of Patent: *Sep. 5, 2000

[54] PROCESS FOR OBTAINING ACTIVE L-α-AMINO CARBOXYLIC ACIDS FROM CORRESPONDING RACEMIC D, L-α-AMINO CARBOXYLIC ACIDS

[75] Inventors: Karlheinz Drauz, Freigericht; Andreas Bommarius, Frankfurt; Michael Karrenbauer, Moss-Bankholzen; Gunter Knaup, Bruchkobel, all of Germany

[73] Assignee: Degussa Aktiengesellschaft, Frankfurt, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 09/094,321

[22] Filed: Jun. 16, 1998

Related U.S. Application Data

[63] Continuation of application No. PCT/EP96/05440, Dec. 13, 1995.

[30] Foreign Application Priority Data

Dec. 13, 1995 [DE] Germany ............................ 195 46 532

[51] Int. Cl.[7] ............................ C12P 41/00; C12P 13/04; C07C 1/00
[52] U.S. Cl. ............................ 435/280; 435/106; 435/108
[58] Field of Search .................................. 435/106, 108, 435/280

[56] References Cited

U.S. PATENT DOCUMENTS 3,841,966  10/1974  Asai et al. ................................... 195/2
4,011,263   3/1977  Wagner et al. ......................... 260/534 S
4,602,096   7/1986  Karrenbauer et al. .................. 548/498

*Primary Examiner*—Sandra E. Saucier
*Attorney, Agent, or Firm*—Omri M. Behr, Esq.

[57] ABSTRACT

The disclosure relates to a process for obtaining optically active L-α-aminocarboxylic acids from the corresponding racemic D,L,α-aminocarboxylic acids. The following steps are involved: (a) the D,L,α-aminocarboxylic acids are acetylated; (b) the N-acetyl-L-α-aminocarboxylic acid present in the mixture of N-acetyl-D,L,α-aminocarboxylic acids thus obtained is broken down enzymatically into the L-α-aminocarboxylic acid; (c) the L-α-aminocarboxylic acid is separated from the mixture, a quantity of a solution of N-acetyl-D(L)-α-aminocarboxylic acids and a quantity of acetate equivalent to the L-α-aminocarboxylic acid being retained; and (d) the N-acetyl-D(L)-α-aminocarboxylic acid is racemized and recycled for enzymatic breakdown. Known extraction processes involving steps (a) to (d) have the disadvantage of producing large quantities of salt. Specifically, the processes are far removed from the ideal equation, according to which one hundred percent of the acetic anhydride and the D,L,α-aminocarboxylic acids are converted to L-α-aminocarboxylic acids and acetic acid. Adjusting the retained solution from step (c) in such a way as to obtain a solution consisting essentially of N-acetyl-D-(L)-α-aminocarboxylic acid salt and free acetic acid in equilibrium with acetate and free N-acetyl-D(L)-α-aminocarboxylic acid and from which acetic acid is extracted by distillation makes it surprisingly easy to feed the solution formed as "mother liquor" following separation of the L-α-aminocarboxylic acid in the circuit and to achieve a materials balance as close as possible to the ideal.

9 Claims, No Drawings

PROCESS FOR OBTAINING ACTIVE L-α-AMINO CARBOXYLIC ACIDS FROM CORRESPONDING RACEMIC D, L-α-AMINO CARBOXYLIC ACIDS

RELATED APPLICATIONS

This application claims priority of PCT Application PCT/EP96/05440 filed Dec. 5, 1996, which claims priority of German Application 1 95 46532.6

FIELD OF THE INVENTION

Process for obtaining optically active l-α-amino carboxylic acids.

BACKGROUND OF THE INVENTION

In accordance with JP OS 138603/76 a workup comprises, among other things, the post-acetylation of free L-α-amino carboxylic acid and subsequent racemization of the post-acetylated mixture by addition of approximately equal mol amounts of acetic anhydride and heating a solution of the thus prepared mixture. The isolation of the relatively insoluble N-Acetyl-D,L-α-amino carboxylic acids can take place by acidification and suitable separation, for example, by filtration.

A more advantageous procedure is described in DE 37 02 689 which comprises the workup of the mother liquors from the enzymatic splitting. In this case, the L-α-amino carboxylic acid can be completely separated. As described in EP-A-O 175 840 the racemization of the free N-Acetyl-D(L)-α-amino carboxylic acid can proceed in a melt with catalytic amounts of acetic anhydride. By solution of the racemized N-Acetyl-D,L-α-amino carboxylic acids in aqueous sodium hydroxide there results a mixture which can again be subjected to acetylase splitting.

In accordance with the procedure of JP OS 138603/76 it is a particular disadvantage that for the therein described racemization of N-Acetyl-D(L)-α-amino carboxylic acids, approximately equal molar amounts of acetic anhydride are required.

There is a further substantial disadvantage in that the N-Acetyl-D,L-α-amino carboxylic acid is recovered through crystallization.

The known workup methods of DE 37 02 689 or EP-A-O 175 840 are likewise burdened with disadvantages in many ways. Thus, during the workup of the mother liquor by means of an ion exchanger, the N-Acetyl-D(L)-α-amino carboxylic acid is eluted as an aqueous solution which contains an amount of acetic acid corresponding to the sodium acetate. Because of the acid pH value of this solution, during the subsequent condensation there is a small amount of hydrolysis to the free amino carboxylic acid which, during the subsequent racemization leads to a higher formation of acyldipeptide. Also the racemization described in EP-A 0 175 840 of free N-Acetyl-D(L)-α-amino carboxylic acids in the melt with catalytic amounts of acetic anhydride leads to the formation of acetyldipeptides.

BRIEF SUMMARY OF THE INVENTION

The invention is concerned with a process for obtaining optically active L-α-amino carboxylic acids from the corresponding D,L-α-amino carboxylic acids. In particular, the invention is concerned with a process in which a) The D,L-α-amino carboxylic acid is acetylated;

b) the N-acetyl-L-α-amino carboxylic acid present in the thereby obtained in N-Acetyl-D,L-α-amino carboxylic acid mixture is enzymatically split into the L-α-amino carboxylic acid;

c) the L-α-amino carboxylic acid is separated from the mixture to yield a solution retaining, among other things, N-Acetyl-D(L)-α-amino carboxylic acid and an amount of acetate equivalent to the thus formed L-α-amino carboxylic acid and d) the N-Acetyl-D(L)-α-amino carboxylic acid contained in the solution is racemized and recycled to enzymatic splitting.

The stereospecific splitting of N-Acetyl-D,L-α-amino carboxylic acids by aminoaceylases is one of the most effective procedures for the preparation of optically active L-amino acids starting from the corresponding racemic D,L-α-amino carboxylic acids.

These procedures can be assembled essentially and especially from the following partial steps;

1) Formation of a racemic mixture of N-Acetyl-D,L-α-amino carboxylic acids from the racemic D,L-α-amino carboxylic acid.

The most practical procedure for the acetylation of α-amino carboxylic acids in accordance with the state of the art is the Schotten-Baumann-acetylation. Herein an aqueous solution of D,L-α-amino carboxylic acid is reacted with acetic anhydride or acetyl chloride under basic conditions. The isolation of N-Acetyl-D,L-α-amino carboxylic acids proceeds by filtration or extraction after acidification.

2) Enzymatic splitting of the N-Acetyl-D,L-α-amino carboxylic acids obtained in the racemic mixture.

For the enzymatic splitting the D,L-α-amino carboxylic acids are generally dissolved in water together with a base suitably, aqueous sodium hydroxide and brought to a pH of between about 6 and 8, that is to say, they are converted into the salts of the corresponding carboxylic acid. With the aid of acetylase the N-Acetyl-D,L-α-amino carboxylic acids then are selectively split into acetate and the L-α-amino carboxylic acid. There results from this reaction, a solution which comprises in addition to acetate and the acetylase among other things, the desired end product namely, the L-α-amino carboxylic acid and also the unreacted N-Acetyl-D(L)-α-amino carboxylic acids, as well as, the salt. The written designation N-Acetyl-D(L)-α-amino carboxylic acids signifies a mixture which comprises principally N-Acetyl-D-α-amino carboxylic acids and lesser amounts of unsplit N-Acetyl-L-α-amino carboxylic acid.

3) Separation of the L-α-amino carboxylic acids and the N-Acetyl-D(L)-α-amino carboxylic acids.

For obtaining the desired product it is necessary to separate it out of the mixture obtained in the previous step. In the case of amino acids relatively insoluble in water such as, for example, phenylanaline, tryptophane, methionine, valine, this can, for example, occur by filtration after concentration or by filtration after carrying out the procedure in a concentrated manner.

4) Racemization and recycling of unreacted N-Acetyl-D-α-amino carboxylic acids.

From the economic and ecological aspect it is not only necessary to isolate the L-α-amino carboxylic acids, but also the N-Acetyl-D(L)-α-amino carboxylic acids and under certain circumstances the enzyme as well and to recycle the same. The separation of the enzyme can occur either through ultrafiltration of the reaction solution, or in the more concentrated procedure by ultrafiltration of the mother liquor after the L-α-amino carboxylic acid was isolated. In the alternative it is also possible if longer reaction times are to be tolerated, to reduce the amount of enzyme charged to such an extent that separation thereof can be entirely avoided.

However, in general the racemization and the recycling of the unreacted N-Acetyl-D,(L)-α-amino carboxylic acids must be maintained. For the workup of the mixture remaining after the isolation of the N-α-amino carboxylic acids the state of the art provides a number of suggestions.

In addition to further components, the mixture contains salts of the unreached N-Acetyl-D(L)-α-amino carboxylic acids, acetate and the remainder of the L-α-amino carboxylic acid

DESCRIPTION OF THE PREFERRED EMBODIMENTS

In all of the described procedures it is necessary for the recycling of the N-Acetyl-D(L)-α-amino carboxylic acids to convert the salts present in the mother liquor into free acids which invariably is connected with salt accumulation.

In view of the hereintofore described problems and the herein named and discussed state of the art, the task of the present invention is to attempt to provide a procedure for obtaining optically active L-α-amino carboxylic acids from the corresponding racemic D,L-α-amino carboxylic acids in such a manner that a recycling of all charged materials is possible wherein, above all, a drastic reduction of salt presence is sought. In particular, in the process in accordance with the present invention, one seeks to approach the ideal equation in which acetic anhydride and D,L-α-amino carboxylic acids are totally converted to L-α-amino carboxylic acids and acetic acid.

The present tasks are solved by a procedure of the previously mentioned type having the characteristics of the characterizing part of claim 1. Useful further embodiments of the invention are placed under protection of the subclaims dependent upon claim 1.

Because of the fact that the retained solution from step (c) is so arranged that a solution basically comprising N-Acetyl-D(L)-α-amino carboxylic acid salt and free acetic acid in balance with acetate and free N-Acetyl-D(L)-α-amino carboxylic acid is obtained from which acetic acid is removed by distillation. It is thus possible, in not in generally foreseen ways, to obtain the desired goal of the invention namely, substantially approaching a materials balance in accordance with the ideal proposal.

As indicated, from a solution comprising only N-Acetyl-D(L)-α-amino carboxylic acid salt and free acetic acid in balance with acetate and free N-Acetyl-D(L)-α-amino carboxylic acid, optically active L-α-amino carboxylic acid can basically be obtained by procedures generally known to those skilled in the art. In the simplest case, the retained solution obtained in step (c) can be considered such a mother liquor.

In case the separation of the L-α-amino carboxylic acid from the mixture of step (c) cannot be fully carried through. The L-α-amino carboxylic acid remaining in the solution must then be post-acetylated. In order not to further raise the amount of acetate remaining in the solution (mother liquor) the post-acetylation is desirably carried out without addition of a base. This means that preferably with the first post-acetylation there is obtained an aqueous solution which basically only comprises N-Acetyl-D(L)-α-amino carboxylic acid salt, acetate and acetic acid.

With respect to the cation of the salt, one is concerned with the counter ion of the base required for the pH adjustment in step (b). In principle it is possible to use, among others, alkali, alkaline earth and ammonium. From the point of view of expense, sodium as the counter-ion in N-Acetyl-D(L)-α-amino carboxylic acid salt as well as in the acetate, is advantageous.

Since the post-acetylated solution, because of separation of the L-α-amino carboxylic acid, contains too small a concentration of N-Acetyl-D,L-α-amino carboxylic acid relative to the sodium acetate content, it is desirable that the solution, after post-acetylation and before concentration has added thereto an amount of N-Acetyl-D,L-α-amino carboxylic acid equal molar to the amount of separated L-α-amino carboxylic acid. After the addition of an amount of N-Acetyl-D,L-α-amino carboxylic acid corresponding to the amount of L-α-amino carboxylic acid isolated, there is obtained a solution which formally comprises a salt of the N-Acetyl-D(L)-α-amino carboxylic acid and acetic acid, which depending on the acidity of the acids, exists in balance with the free N-Acetyl-D(L)-α-amino carboxylic acid and the corresponding salt of acetic acid.

In the framework of the present invention there is a particularly favorable mode of proceeding characterized thereby that to the solution before removal of acetic acid by distillation, an amount of N-Acetyl-D,L-α-amino carboxylic acid, eqimolar to the removed Lα-amino carboxylic acid is added and the solution is brought to a pH of between 3 and 8, preferably of between 4.5 and 5.5 and condensed to a melt. To achieve this it is preferable to evaporate under vacuum in a temperature range of between 100 to 220° C. Preferred are temperatures between 130 and 180° C. In those cases in which the salts (preferably sodium salts), of the N-Acetyl-D(L)-α-amino carboxylic acids have a relatively high melting point that is to say, over 200° C. Temperatures below the melting temperature are sufficient, since even in a mixture of N-Acetyl-D(L)-α-amino carboxylic acid and acetate salts as solids, in a vacuum acetic acid may be distilled off under the formation of salts of N-Acetyl-D(L)-α-amino carboxylic acids.

The post-acetylation already discussed hereinabove may be usefully so carried out that the N-Acetyl-D,L-α-amino carboxylic acids are transferred into a aqueous medium for enzymatic splitting and that the solution before carrying out step (d) for the post-acetylation of the L-α-amino carboxylic acid still remaining therein without addition of further base there are added at least 1.1 mole equivalents of acetic anhydride relative to the remaining amount of L-α-amino carboxylic acid. It is thus possible in a stunningly simple manner to achieve a cyclic use of the solution remaining as a mother liquor after the separation of the L-α-amino carboxylic acid.

Within the framework of the invention it was astonishingly found that the solution which results as the mother liquor from a further embodiment of the process, in which the L-α-amino carboxylic acid liberated by the acylase is isolated by filtration after concentration, or by filtration after operating in a concentrated mode and which contains besides the N-Acetyl-D(L)-α-amino carboxylic acid salt, an amount of acetate eqimolar to the amount of L-α-amino carboxylic acid formed, as well as, the remainder of the L-α-amino carboxylic acid, without separation of the remaining L-α-amino carboxylic acid and without separation of the acetate may be brought into a form which can be used directly in the acetylase splitting. Thus, obtaining of optically active L-α-amino carboxylic acids from the corresponding racemic D,L-α-amino carboxylic acid can take place substantially more efficiently.

The solution resulting as mother liquor and to be again treated for actylase splitting in accordance with the present invention can thus have a changing composition. Thus, one may be concerned with the mother liquor and a solution obtained during the first approach of the process. It is however, equally possible that the solution is a mother liquor obtained after several circuits of the process. Furthermore, the mother liquor can also comprise such solutions which occur by the combination of different solutions, for example, coming from different splitting solutions obtained from parallel enzymatic splitting steps.

In any case there is a particularly preferred composition. In fact, after particular handling it comprises a particular form. The particular treatment comprises an adjustment of the solution with a base to a pH value of between 4 and 8 so that the N-Acetyl-D,L-α-amino carboxylic acids are available in aqueous solution in the form of their salts. It is advantageous for the pH value to lie between 6 and 8. It is useful to utilize dilute aqueous sodium hydroxide solution for the adjustment of the pH value. The treatment comprises the selective enzymatic splitting of N-Acetyl-L-α-amino carboxylic acid and the separation of L-α-amino carboxylic acids. Directly after the treatment, that is to say, at a point in time dependent upon the separation of the L-α-amino carboxylic acid, the mother liquor comprises a solution with preferably up to 5 wt % of unseparated L-α-amino carboxylic acid, up to 40 wt % N-Acetyl-D(L)-α-amino carboxylic acid salt and up to 15 wt % of acetate wherein, these weight references are relative to the total weight of aqueous solution (mother liquor).

A further aspect of the process in accordance with the present invention may comprise the conversion of the N-Acetyl-D,L-α-amino carboxylic acid provided to the process into the sodium salt under utilization of sodium acetate contained in the mother liquor.

This is possible, since it was surprisingly found within the framework of the present invention that it is possible to almost entirely distill off the acetic acid from a solution comprising equal molar amounts of N-Acetyl-D,L-α-amino carboxylic acid and sodium acetate without the occurrence of disadvantageous side reactions.

In order to apply this procedure the mother liquor resulting from the racemate splitting, it is at first necessary to acetylate all of the free amino acid present in the mother liquor.

It has been found particularly useful and particularly profitable to carry out the post-acetylation when this requires the addition of at least 1.5 equivalents and preferably between 1.7 and 1.0 equivalents of acetic anhydride relative to the amount of L-α-amino carboxylic acid remaining in the solution, without the addition of a base.

If the post-acetylation is carried out with less than 1.1 equivalents of added acetic anhydride there is the danger of an incomplete conversion of the L-α-amino carboxylic acid (salts) into the N-Acetylated composition. If more than 3 equivalents are utilized, the material balance is unfavorable, since too much acetic anhydride remains unused. Furthermore, the danger of undesired side reactions is substantially greater.

Since the goal of the present invention is a cyclic utilization of all materials, after separation of the acetic acid the remaining materials mixture can be further processed. It is particularly advantageous if the resulting salt of N-Acetyl-D(L)-α-amino carboxylic acid is racemized after concentration and without further addition is dissolved in water and recycled to the enzymatic racematic splitting. In contrast to the till now known modes of proceeding, the variant in accordance with the present invention, has the great advantage that the sodium ions must not first be separated out which generally occurs with the salt of a mineral acid whereby, the separated sodium mineral acid salts must be disposed of via waste waters. Furthermore, the procedures of the present invention avoids the new formation of salt which is provoked by the procedures of the literature, that in the course of neutralization of the N-Acetyl-D(L)-α-amino carboxylic acids new sodium ions are brought into the system. In contrast to the workup via an ion exchanger, the procedures of the present invention have the further advantage that during evaporation of the sodium salt, that is to say, at a pH value of between 3 and 8 compared with the evaporation of the N-Acetyl-D(L)-α-amino carboxylic acid/acetic acid mixture which have a pH value of about 2, the hydrolysis of the amino carboxylic acid is substantially reduced and the production of byproducts is reduced.

The racemization of the N-Acetyl-D(L)-α-amino acid salt resulting from the procedures of the present invention is basically possible in all of the modes known to one skilled in the art. Preferred is the formation of a melt by heating at temperature higher than room temperature, preferably under the addition of catalytic amounts of acetic anhydride. In comparison to the racemization procedures of free N-Acetyl-D(L)-α-amino acids described in EP 0 175 840 there is substantially less byproduct (in particular, acetylated di-peptide).

Furthermore, it is possible to carry out, in solution, the racemization of Acetyl-D(L)-α-amino acid salts as described in JP OS 138603/76.

In this case the racemization is most advantageously carried out before the addition of the N-Acetyl-D,L-α-amino acid and before concentration to a melt.

The procedure of the present invention can also be advantageously carried out in the workup of an aqueous solution of N-Acetyl-D(L)-α-amino acid and acetic acid eluted from an ion exchanger.

After the timely neutralization in accordance with the state of the art after racemization (after completion of the reaction time) by quenching with aqueous alkali metal hydroxide or ammonia solution has been achieved. With the conversion of at least a part of the N-Acetyl-D(L)-α-amino carboxylic acid into the appropriate salt, together with a reduction of the hydrolysis during evaporation, also through the thus connected change of the composition of the mixture to be racemized, is responsible in a not foreseeable manner for a desirable condition with respect to byproduct production.

In particular one can suspect that this may be related to a substantially elevated thermal stability of the salt in comparison to the free acetyl amino acid.

In the framework of the invention the racemization of the N-Acetyl-D(L)-α-amino carboxylic acid salt or a mixture which comprises this salt together with the corresponding free acid can be particularly usefully carried out in a "non-aqueous" condition. In accordance with the invention, this may be understood to mean that racemization is not to be carried in aqueous solution. The absolute absence of water however, as mentioned above, is not a prerequisite for the successful carrying out the procedure in accordance with the present invention.

By conversion of at least a part of the N-Acetyl-D(L)-α-amino carboxylic acid into the corresponding N-Acetyl-D(L)-α-amino carboxylic acid salt is understood that there is, during the racemization itself there is a result, a mixture of free acid and salt or salt only.

In so far as a mixture of salt and acid is utilized for the racemization the racemization mixture may be obtained by mixing of the corresponding pure materials.

In a preferred embodiment in accordance with the present invention, an aqueous solution of N-Acetyl-D(L)-α-amino carboxylic acid, or if desired, also in the presence of acetic acid, is reached with a base preferably sodium hydroxide. Herein a pH value is obtained or set which does not lie over 8.

Suitably, an aqueous solution of the N-Acetyl-D(L)-α-amino carboxylic acid or an aqueous solution containing this mixed with the appropriate N-Acetyl-D(L)-α-amino carboxylic acid salt is set to a pH value of 2 to 8 preferably 4 to 8 in particular, 4.5 to 5.5.

By setting to a predetermined pH range or value not only is a substantial quantity of the free acid converted to the corresponding salt, at the same time by the thus set conditions a useful condition of the desirable reaction speed for thermal racemization is obtained. By setting the value of the pH of the process of the present invention to a value of between 2 to 8, suitably 4 to 8, preferably 4.5 to 5.5 the danger of hydrolysis of the N-Acetyl-D(L)-α-amino carboxylic acid salt in comparison to the free Acetyl amino carboxylic acid is substantially reduced and with it also byproduct formation (N-Acetyl Dipeptide) so that even longer reaction times at higher temperatures have substantially no negative effect on the yield. The pH value is desirably set at 4.5 to 5.5, since in this pH range the buffer effect of the mixture is at its greatest.

In order to adjust its pH to the desired value one may utilize basically any base available to one skilled in the art which can form salts with N-Acetyl-D(L)-α-amino carboxylic acids. Especially preferred are aqueous alkaline hydroxides. Particularly preferred is sodium hydroxide because the pH setting with aqueous sodium hydroxide is essentially made easier on the technical scale.

A solution adjusted with a base to the pH value range of the present invention, in a desirable procedural modification, is evaporated to dryness with the obtaining of a residue which may be either solid or a melt.

This is advantageous when the thus obtained residue whether a melt or a dried solid is treated with acetic anhydride for racemization by heating.

Where one is concerned with a melt, as the substance to be racemized, the addition of a catalytic amount of acetic anhydride is preferred, since thereby the speed of racemization is substantially increased.

The melting of the N-Acetyl-D(L)-α-amino carboxylic acid and the heating of the melt preferably proceeds under nitrogen. The melting and the heating of the melt can however, be carried out without a protective gas or in vacuum.

Although, the utilization of melt for racemization is very advantageous it has furthermore unexpectedly been shown that for the completion of a process of the present invention for racemization it is not absolutely necessary to obtain a melt of acetyl amino acid salt. In the circumstance that the melting point of the salt lies very high it is possible to mix the solid with the appropriate amount of acetic anhydride and to heat this mixture under the melting point of the acetyl amino acid salt. By the addition of the acetic anhydride a partial melt may form which is sufficient for the racemization.

In accordance with this procedure, for example, acetyl-phenylalanine sodium and acetyl-valine-sodium can already be racemized at 160° C.

The quantity of acetic anhydride to be added is not critical within the framework of the present invention. Preferably, one utilizes a melt or a partial melt under good admixing of between 2 and 10 wt % particularly preferred being 2 to 10 wt % of acetic anhydride with reference to the sum of the N-Acetyl-D(L)-α-amino carboxylic acid and N-Acetyl-D (L)-α-amino carboxylic acids salt.

The temperature that is utilized to carry out the racemization should be as high as possible without unduly damaging the substances, or permitting side reactions to come into the foreground.

If, under these conditions, it is possible to obtain a melt so it is advantageous for the melt to be racemized to be heated to and at a temperature which lies from 5 to 10° C. over the melting point of the respective N-Acetyl-D(L)-α-amino carboxylic acid or the salt pertaining thereto whichever temperature is higher.

If, for reason of the melting point of the substances taking part in the reaction it is not possible to obtain a total melt, it is advantageous to choose a temperature for racemization in the range of 100 to 220° C. preferably, 130 to 180° C., these ranges generally meet all of the necessary requirement.

For the further processing of the racemate one can use all embodiments heretofore available to one skilled in the art. Preferably the melts or partial melts, after completion of the heating are taken up in water and then subjected to further processing. In accordance with the procedures of the present invention a large number to the successfully obtainable compositions belong, among others, compounds of Formula I

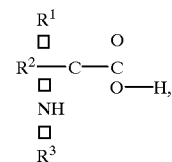

wherein
R$^1$ is hydrogen or C$_{1-4}$ alkyl,
R$^2$ is hydrogen, alkyl, substituted alkyl, aryl, substituted aryl, heteroaryl, aralalkyl, heteroaralalkyl, cycloalkyl, or cycloalkylalkyl, wherein the named residues of themselves may either be substituted and/or contained heteroatoms therein, or
R$^1$ and R$^2$ taken together with the carbon atom to which they are attached may be formed into a 3–7 membered saturated ring,
R$^3$ may be hydrogen or C$_{1-4}$ alkyl, or
R$^2$ and R$^3$ when taken together with the nitrogen and the carbon atom to which they are attached, may form a 4–7 membered saturated ring which may contain a heteroatom.

With respect to R$^2$, the alkyl groups may be straight or branch chained and suitably have a chain length of C$_1$–C$_{12}$ for the straight chains and C$_3$–C$_{12}$ with the branch chains, particularly preferred are chain lengths of C$_1$–C$_6$ for straight chains and C$_3$–C$_6$ with branch chains. As illustrations but not as limitations, there may be cited methyl, ethyl, propyl, isopropyl, butyl, isooctyl and dodecyl.

The aforementioned alkyl groups may be substituted by 1–3 amino groups, hydroxyl, halo, guanidino, ureiodo, carboxy, carboxamido and/or alkoxy groups wherein the alkyl moiety thereof is as set forth above.

Aryl is suitably phenyl or substituted phenyl wherein the substituent groups are as set forth above with respect to alkyl.

Substituted aryl groups are suitably mono-, di-, or trihalo, mono-, di-, or trihydroxy, mono-, di- or trialkyl phenyl groups, wherein suitably halogen is fluoro, chloro or bromo and alkyl is $C_1$–$C_4$ alkyl, suitably methyl or ethyl.

As heteroalkyl groups there are preferred 5 or 6 ring systems with 1–2 heteroatoms in the ring, suitably oxygen, nitrogen, or sulfur.

As an aralkyl group, benzyl is preferred and cycloalkyl and cycloalkyl methyl, suitably $C_{3-7}$ ring systems.

Especially preferred as compounds falling within the above group are alanine, valine, leucine, isoleucine, proline, tryptophan, phenylalanine, methionine, serine, tyrosine, threonine, cysteine, asparagine, glutamine, histidine, cystine, citrulline, homocysteine, homoserine, hydroxyproline, ornithine and norvaline, as well as the derivatives of the foregoing amino acids Particularly preferred are N-acetyl-D(L)-methionine, -valine, -phenylalanine, and/or norvaline.

The invention may be further explained by the following examples. All percent data unless otherwise indicated mean wt %.

EXAMPLE 1

Preparation of N-Acetyl-D,L-methionine

Different quantities of D,L-methionine were dissolved in 100 ml acetic acid the solution warmed in an oil bath and 1.1 equivalence of acetic anhydride were added. After 5 minutes the components were concentrated under vacuum at 100° C. bath temperature. The content of N-Acetyl-D,L-methionyl-D,L-methionine (Ac-Met-Met) was determined by HPLC. the results of these experiments are set forth in the following table.

| D,L-Methionine | Acetic Acid | Acetic Anhydride | Temp | Ac-Met-Met |
|---|---|---|---|---|
| 7.5 g (50 mmol) | 100 ml | 5.6 g (55 mmol) | 80° C. | 1.8% |
| 7.5 g (50 mmol) | 100 ml | 5.6 g (55 mmol) | 95° C. | 1.8% |
| 14.9 g (100 mmol) | 100 ml | 11.2 g (110 mmol) | 95° C. | 3.2% |
| 26.1 g (175 mmol) | 100 ml | 19.6 g (192 mmol) | 95° C. | 5.9% |
| 37.3 g (250 mmol) | 100 ml | 28.1 g (275 mmol) | 95° C. | 7.8% |

EXAMPLE 2

Production of N-Acetyl-D,L-methionine Under Technical Conditions 373 g (2.5 mol) D,L-methionine were dissolved 5 l acetic acid at 90° C. and treated with 281 g (2.75 mol) acetic anhydride. Thereby the temperature rose to 95° C. After ten minutes post-reaction, the solution was concentrated in a Sambay-evaporator at 170° C. and 9 mbar. A yield of 427 g of a tacky oil was obtained, which solidified on cooling. After HPLC analysis the product was shown to consist of 92.3% Acetyl-D,L-methionine and 3.4% Ac-Met-Met.

EXAMPLE 3

Preparation of N-Acetyl-D,L-valine 11.7 g (0.10 mol) D,L-Valine were dissolved in 100 ml of acetic acid and treated with 11.2 g (0.11 mol) acetic anhydride at 90° C. Concentration was carried out after 10 minutes at 15 mbar and 100° C. After HPCL analysis the crystalline residue was shown to contain 95.6% Acetyl-D,L-valine and 2.8% N-Acetyl-D,L-valyl-D,L-valine.

EXAMPLE 4

Preparation of N-Acetyl-D,L-Norvaline 11.7 g (0.10 mol) D,L-Norvaline were treated in a manner analogous to that set forth in Example 3. The crystalline residue was shown, after HPLC analysis to contain 95.2% N-Acetyl-D,L-Norvaline and 4.1% N-Acetyl-D,L-Norvalyl-D,L-Norvaline.

EXAMPLE 5

Removal of Acetic Acid from a Mixture of N-Acetyl-D,L-Methione and Sodium Acetate In each case 38.2 g (0.20 mol) N-Acetyl-D,L-methionine and 16.4 g (0.20 mol) of sodium acetate were intensively mixed and heated. Above approximately 100° C. melts were formed. The melts were heated at 15 mbar for 30 minutes at between 150 and 180° C. and after cooling the acetic acid content was determined. Results are summarized in the following table.

| Temperature | Acetic Acid |
|---|---|
| 150° C. | 5.3% |
| 160° C. | 4.3% |
| 170° C. | 3.0% |
| 180° C. | 3.0% |

EXAMPLE 6

Removal of Acetic Acid from a Mixture of N-Acetyl-L-Valine and Sodium Acetate 79.6 g (0.50 mol) L-Valine and 41.0 g (0.5 mol) of sodium acetate were dissolved with warming in 150 ml of water and concentrated to dryness at 100° C. and 15 mbar. Portions of the solid residues were subsequently dried for 30 minutes at different temperatures and the acetic acid content determined.

| Temperature | Acetic Acid |
|---|---|
| 100° C. | 10.4% |
| 150° C. | 5.5% |
| 175° C. | 2.1% |
| 200° C. | 1.7% |

EXAMPLE 7

Removal of Acetic Acid from a Mixture of N-Acetyl-L-Phenylalanine and Sodium Acetate 103.6 g (0.50 mol) L-Phenylalanine and 41.0 g (0.5 mol) sodium acetate were dissolved in 150 ml under warming and concentrated to dryness at 100° C. under 15 mbar. Portions of the solid residue were subsequently dried for 30 minutes at different temperatures and the content of acetic acid determined. Results are summarized in the following table.

| Temperature | Acetic Acid |
|---|---|
| 100° C. | 7.3% |
| 150° C. | 3.5% |
| 175° C. | <0.5% |

EXAMPLE 8

Removal of Acetic Acid from a Mixture of N-Acetyl-D,L-Norvaline and Sodium Acetate In each case 3.12 g (0.02 mol) N-Acetyl-D,L-Norvaline and 1.46 g (0.02) sodium acetate were intensively mixed and heated. After about 110° C. a melt is formed. The melt is heated under 15 mbar for 30 minutes at 160° C. After cooling the sample contained 2.2% acetic acid.

EXAMPLE 9

Comparison of the Thermal Stability of N-Acetyl-D,L-Methionine and N-Acetyl-D,L-Methionine Sodium Salt In each case 20 g N-Acetyl-D,L-Methionine and N-Acetyl-D,L-Methionine sodium salt were heated to 150° C. the formation of N-Acetyl-D,L-Methionyl-D,L-methionine was tracked by HPLC. Results are set forth in the following table.

| Time | Ac-Met-OH | Ac-Met-ONa |
|---|---|---|
| 1 h | 1.7% | 0.1% |
| 2 h | 3.8% | 0.2% |
| 5 h | 8.8% | 0.4% |

EXAMPLE 10

Racemization of N-Acetyl-D(L)-methionine-sodium in the Melt

In each case 10 g (0.053 mol) N-acetyl-D(L)-methionine were treated with an 8 wt % solution of aqueous sodium hydroxide at different pH values and concentrated to a melt at 15 mbar. Afterwards, the melts were heated and treated under good stirring with acetic anhydride. These melts were then left at this temperature and subsequently taken up in water. To track the racemization the specific rotation ($[\alpha]_D^{20}$, c=1 in water) was determined. Prior to racemization this specific rotation was 21.3. The results of these experiments are set forth in the following table.

| Value | Ac$_2$O | Temp. | Duration | $[\alpha]D^{20}$ | Ac-Met-Met |
|---|---|---|---|---|---|
| 5 | 2% | 155° C. | 30 min | 0 | 0.3% |
| 4 | 2% | 155° C. | 30 min | +0.2 | 0.8% |
| 6 | 2% | 155° C. | 30 min | 0 | 0.2% |
| 5 | 3% | 110–120° C. | 30 min | +0.5 | 0.05% |
| 5 | 2% | 180° C. | 10 min | 0 | 0.1% |
| 5 | 2% | 180° C. | 30 min | 0 | 0.8% |
| 8 | 3% | 155° C. | 30 min | 0 | 0.4% |
| 5 | 6% | 155° C. | 30 min | 0 | 0.5% |
| 1.6 | 2% | 155° C. | 30 min | 0 | 5.5% |

EXAMPLE 11

Racemization of N-Acetyl-L-phenylalanine Sodium Salt

The samples of N-Acetyl-L-phenylalanine sodium salt prepared in accordance with Example 7 and dried at 150° C. in vacuum were mixed with acetic anhydride and warmed. To track the racemization the specific rotation ($[\alpha]_D^{20}$ c=1 in N HCl) was determined. Before racemization this specific rotation was +21.6. The results are set forth in the following table.

| Ac$_2$O | Temp. | Duration | $[\alpha]D^{20}$ |
|---|---|---|---|
| 2% | 140° C. | 15 min | 9.0 |
| 2% | 160° C. | 15 min | 2.9 |
| 2% | 180° C. | 15 min | 1.9 |
| 5% | 160° C. | 15 min | 0 |
| — | 230° C. | 15 min | 10.8 |

EXAMPLE 12

Racemization of N-Acetyl-L-Valine Sodium Salt

N-Acetyl-L-valine sodium salt prepared in accordance with Example 6 was vacuum dried at 150° C., mixed with acetic anhydride and warmed. Racemization was followed by determining the specific rotation ($[\alpha]_D^{20}$c=1 in 1 N HCl), prior to racemization the specific rotation was 11.9. The results are summarized in the following table.

| Ac$_2$O | Temp. | Duration | $([\alpha]D^{20}$ |
|---|---|---|---|
| 2% | 140° C. | 15 min | 10.2 |
| 2% | 160° C. | 15 min | 6.5 |
| 2% | 180° C. | 15 min | 4.8 |
| 5% | 160° C. | 15 min | 1.6 |
| 5% | 230° C. | 15 min | 0 |
| — | 230° C. | 15 min | 8.3 |

EXAMPLE 13

Post-Acetylation of N-Acetyl-D(L) Methionine Mother Liquor

After removal of the L-methionine by filtration each 100 g of the thus obtained mother liquor which contained per 100 g, 8.3 g (0.100 mol) sodium acetate, 19.3 g (0.089 mol) N-Acetyl-D(L) methionine sodium and 1.7 g (0.011 mol) L-Methionine was treated at different temperatures with different amounts of acetic anhydride. In each case after 30 minutes samples were taken and the methionine content determined by HPLC.

| Temp. | Acetanhydride | Methionine |
|---|---|---|
| 30° C. | — | 9.0 Fl.-% |
| 30° C. | 1.16 g (11.4 mmol) | 2.9 Fl.-% |
| 30° C. | 1.74 g (17.1 mmol) | 1.2 Fl.-% |
| 30° C. | 2.03 g (19.9 mmol) | 0.6 Fl.-% |
| 30° C. | 2.61 g (25.6 mmol) | 0.2 Fl.-% |
| 60° C. | 1.16 g (11.4 mmol) | 2.9 Fl.-% |
| 60° C. | 1.74 g (17.1 mmol) | 0.2 Fl.-% |
| 60° C. | 2.03 g (19.9 mmol) | 0.0 Fl.-% |
| 90° C. | 1.16 g (11.4 mmol) | 2.9 Fl.-% |
| 90° C. | 1.74 g (17.1 mmol) | 0.3 Fl.-% |
| 90° C. | 2.03 g (19.9 mmol) | 0.1 Fl.-% |

EXAMPLE 14

Recycling of an N-Acetyl-D(L)-Methionine Sodium Salt Mother Liquor 717 g (3.75 mol) N-Acetyl-D,L-Methionine and 140 g (3.50 mol) sodium hydroxide were dissolved in water and made up to 1.5 liters. The pH value was adjusted to 7 with 50% aqueous sodium hydroxide solution. After addition of 3.6 g acylase (activity 31.000 E/g), the mixture was stirred for 5 days at room temperature. The suspension was cooled to 5° C. and the precipitate filtered off, washed with 300 ml of ice water and dried. There was obtained 174 g (1.17 mol) L-methionine. The filtrate (1800 g) which contained, in addition to 21.8 wt % N-Acetyl-D(L)-Methionine, 2.8 wt % L-Methionine was warmed to 60° C. and treated with 6 g (0.60 mol) acetic anhydride. After 30 minutes no methionine was detectable in the solution. There was added 223 g (1.17 mol) N-Acetyl-D,L-Methionine and concentrated under vacuum to 1200 g. The solution was concentrated to 752 g in a Sambay-evaporator under 170° C. and 10 mbar. Into the still warm melt were added 15 g of acetic anhydride, heated for 10 minutes at 140° C., then this was dissolved in water and made up to 1.5 liters. The specific rotation of the solution was 0. The content of N-Acetyldipeptide amounted to 0.8% relative to N-Acetyl-methionine. After the pH value was adjusted to 7 with aqueous sodium hydroxide as described above, acylase splitting was again carried out. The yield was 166 g (1.11 mol) L-Methionine.

EXAMPLE 15

Recycling of N-Acetyl-D(L)-Norvaline Sodium Salt Mother Liquor 597 g (375 mol) N-Acetyl-D,L-Norvaline and 140 g (3.50 mol) sodium hydroxide were dissolved in water and made up to 1.5 liters. The pH value of the solution was brought to 7 with 50% aqueous sodium hydroxide. After addition of 3.0 g acylase (activity 31.000 E/g) stirring was continued for 5 days at room temperature. The suspension was cooled to 5° C. and the precipitate filtered off, washed with 300 ml ice water and dried. There was obtained 157 g (1.34 mol) L-Norvaline. The filtrate which contained, besides 22.5 wt % N-Acetyl-D(L)-Norvaline, 3.1 wt % L-valine, was warmed to 60° C. and treated with 64 g (0.62 mol) acetic anhydride. After 30 minutes no norvaline was detectable in the solution. 213 g ((1.34 mol) N-Acetyl-D,L-Norvaline were added and concentrated in vacuum to 950 g. The solution was concentrated in a Sambay-evaporator at 170° C. and 10 mbar to 644 g. Into the still hot melt were stirred 13 g of acetic anhydride, heated for 10 minutes at 140° C. and dissolved in water and made up to 1.5 liters. Chromatographic ee-determination gave a D/L relationship of 51.3 to 48.7%. The content of N-Acetyldipeptide was 1.2% relative to N-Acetyl-norvaline. After the pH was adjusted to 7 with aqueous sodium hydroxide this solution was subjected to further acylase splitting as described above. There is obtained 113 g (0.97 mol) L-Norvaline. Fl. –% means the percentage of the area under the HPLC curve relating to the peak for methionine.

Further advantages and embodiments of the invention may be determined from the following patent claims.

What is claimed is:

1. A process for obtaining an optically active L-alpha-amino acid from the corresponding racemic D,L-alpha-aminocarboxylic acids comprising the steps of
   a) chemically acylating the said D,L-alpha-aminocarboxylic acids to produce N-Acetyl-D,L-alpha-aminocarboxylic acids;
   b) adding sufficient base to bring said N-Acetyl-D,L-alpha-aminocarboxylic acids to a pH range of between about 6 and 8 and preferentially deacylating the N-Acetyl-L-alpha-aminocarboxylic acid present in the mixture using a stereo specific acylase to form a composition comprising L-alpha-aminocarboxylic acid, an equimolar amount thereto of acetate, N-Acetyl-D-alpha-aminocarboxylic acid salt and a lesser amount of N-Acetyl-L-alpha-aminocarboxylic acid salt;
   c) separating the composition formed in step (b) into a first fraction containing most of the L-alpha-aminocarboxylic acid and a second fraction comprising N-Acetyl-D-alpha-aminocarboxylic acid salt and an amount of acetate equivalent to the L-alpha-aminocarboxylic acid formed
   d) adding to said second fraction an amount of N-Acetyl-D,L-alpha-aminocarboxylic acid equivalent to the removed L-alpha-aminocarboxylic acid, then removing the acetic acid formed by distillation;
   e) racemizing the mixture of step (d);
   f) subjecting the racemized mixture to the specific deacylation procedure of step (b).

2. The process in accordance with claim 1 comprising the steps of concentrating the solution of step (d) to a melt at a pH of between 4.5 and 5.5.

3. The process in accordance with claim 2 comprising racemizing the product obtained after concentration and recycling same to enzymatic deacylation.

4. The process in accordance with claim 1 comprising racemizing the N-Acetyl-D-α-aminocarboxylic acid as salt or in a mixture together with free acid in the presence of from 1 to 10 wt % of an acetic anhydride at 100–200° C.

5. Process in accordance with claim 4 comprising racemizing at temperatures between 130 and 180° C.

6. Process in accordance with claim 1 wherein prior to step (e) the concentrated second fraction is treated with at least 1.1 mol equivalents of acetic anhydride related to the unseparated amount of L-α-amino carboxylic acid present.

7. Process in accordance with claim 6 comprising treating the solution for the acetylation of the unseparated L-amino carboxylic acid with up to 3 equivalents of acetic anhydride relative to the unseparated L-α-amino carboxylic acid at a pH of between 4 and 8 prior to subjecting the resulting solution to enzymatic splitting.

8. Process in accordance with claim 1 wherein the starting materials are selected from the group consisting of D,L-methionine, valine, phenylalanine and norvaline to yield the corresponding L-methionine, valine, phenylalanine and norvaline.

9. The process of claim 1 for obtaining an optically active L-alpha-amino acid from the corresponding racemic D,L-alpha-aminocarboxylic acids comprising the additional steps of
   c') acetylating the L-alpha-aminocarboxylic acid present in the second fraction of step (c);
   d') adding to said second fraction acetylated in step c') an amount of N-Acetyl-D,L-alpha-aminocarboxylic acid equivalent to the removed L-alpha-aminocarboxylic acid, then removing the acetic acid formed by distillation;
   e) racemizing the mixture of step (d');
   f) subjecting the racemized mixture to the specific deacylation procedure of step (b).

* * * * *